Figure 1:
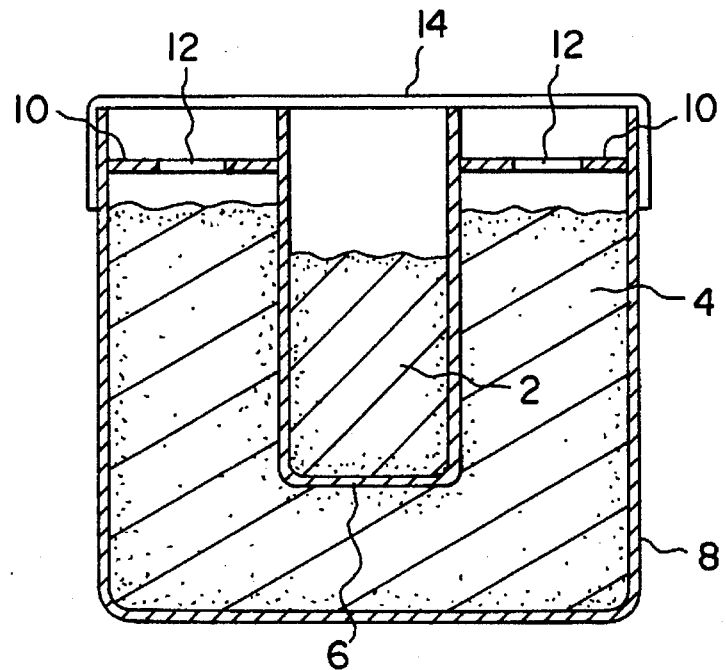

United States Patent
Matsumoto et al.

[11] Patent Number: 5,593,635
[45] Date of Patent: Jan. 14, 1997

[54] METHOD FOR PERFUMING CONVEYANCES AND PERFUMING ARTICLE THEREFOR

[75] Inventors: Noritsune Matsumoto; Kazuo Kamitani, both of Hyogo, Japan

[73] Assignee: F. Cube Co. Ltd., Hyogo, Japan

[21] Appl. No.: 510,865

[22] Filed: Aug. 3, 1995

[30] Foreign Application Priority Data

Aug. 5, 1994 [JP] Japan .................................. 6-204645

[51] Int. Cl.$^6$ .................. A61L 9/02; A61L 9/03
[52] U.S. Cl. ............... 422/5; 422/120; 422/125; 126/263.05
[58] Field of Search ............... 422/5, 120, 125; 126/59.5, 263.04, 263.05

[56] References Cited

U.S. PATENT DOCUMENTS

| | | | |
|---|---|---|---|
| 2,497,612 | 2/1950 | Katzman | 422/125 |
| 3,675,637 | 7/1972 | Trimble | 126/263.05 |
| 4,171,340 | 10/1979 | Nishimura et al. | 422/36 |
| 4,330,506 | 5/1982 | Takei | 422/125 |
| 4,338,098 | 7/1982 | Yamaji | 126/263.05 |

FOREIGN PATENT DOCUMENTS

| | | |
|---|---|---|
| 22-14343 | 8/1947 | Japan . |
| 60-130501 | 7/1985 | Japan . |
| 60-55481 | 12/1985 | Japan . |
| 9107996 | 6/1991 | WIPO .................................. 422/125 |

OTHER PUBLICATIONS

Derwent Publications Ltd. London, GB, JP-A-54 002 330.

Primary Examiner—Robert J. Warden
Assistant Examiner—Theresa T. Snider
Attorney, Agent, or Firm—Nikaido, Marmelstein, Murray & Oram LLP

[57] ABSTRACT

A mixture of an oily fragrance liquid, an oily disinfestant and an organic blowing agent is heated by the heat of the reaction between calcium oxide and water, and the fragrance liquid is atomized by the blowing gas stream and made to adhere to the interior of the conveyance.

10 Claims, 1 Drawing Sheet

METHOD FOR PERFUMING CONVEYANCES AND PERFUMING ARTICLE THEREFOR

FIELD OF THE INVENTION

The present invention relates to perfuming or scenting conveyances such as automobiles, buses, airplanes, boats and rail cars, and in particular, to reproducing the scent of new conveyances. The present invention particularly relates to refreshing the smell of used automobiles to that of new ones.

PRIOR ART

Every new vehicle (conveyance) has its own scent unique to it. Such a scent differs for different kinds of conveyances, and especially from manufacturer to manufacturer of a conveyance. The scent is composed of odors of the components of a conveyance and odors originating from the assembly plant of the conveyance. For instance, some automobile manufacturers have been introducing aromas of flowers to their assembly plants to scent new automobiles with aromas of flowers. Some other automobile manufacturers do not give any special consideration to the smells of their automobiles. As a result, the scents of the automobiles are directly composed of odors of components and those of the atmospheres of the plants. Apart from the special scents such as those of flowers, the scent of a conveyance is mainly composed of the aromas of leather products such as seats, and of odors of organic solvents originating from plastic boards, lubricants, heat insulators, adhesives, etc., and the scent is determined by the odors of the conveyance components used and the odors of the assembly lines of the assembly plant. Kinds of scent differ significantly from manufacturer to manufacturer of a conveyance. For instance, there is a big difference between the scent of a conveyance, of which manufacturer perfumes their products with aromas of flowers, and the scents of products of other manufacturers. Even for the same manufacturer, there are some differences in scents of products from one assembly plant to another. For instance, there are some differences in scents between new products of an European plant and those of a U. S. plant of one identical manufacturer. In this case, there is not much difference from one vehicle kind to another. The scents are almost identical among various kinds of vehicle provided they are produced by the same manufacturer or plant. Differences in scent from one vehicle kind to another arise from the presence or absence of aroma of leather. Highgrade conveyances have leather seats whereas those of common make have fabric seats. The scents of new products of conveyances will be lost within several months. After that, the odors of the users will become dominant.

Conveyances, and in particular, automobiles are traded in used car markets. In a used car market, automobiles are cleaned, their interiors and coatings are refurbished before trading, to restore them as close to the new conditions as possible. However, much attention has not been given to the scents of automobiles. There are only some cases in which used cars are disinfected before trading, and the cars eventually acquire an odor of a disinfectant. Hence used cars are clearly different, in the aspect of scents, from new cars. In the sensory aspect, scents are important elements of value of an automobile, but this fact scarcely has been recognized to the present.

Now, let us examine related prior arts. It is well known to impregnate a fabric sheet or the like with an odoriferous substance and hang it in a vehicle so as to release the fragrance gradually. The kinds of scents employed are scents of flowers, aroma of lemon, etc. They, however, do not reflect, in any sense, the scents of new cars. Suppose that a fabric sheet is impregnated with some odoriferous substances to gradually evaporate them so as to reproduce the scent of new car. This process itself is not scenting the automobile with the scent of new automobile. In this case, the scent of new automobile arises not from the automobile itself but the sheet impregnated with the odoriferous substances, and the automobile itself is not refreshed in the aspect of scent to the conditions of a new automobile. The user, for instance, may sense that the scent comes from the fabric sheet and it is not the scent of the automobile itself. The user will feel that the scent is a fake one not the genuine scent.

Another prior art technique is to atomize a disinfestant in the form of a mist by entraining it in a stream of vapor of a blowing agent so as to disinfest houses and buildings. For example, Japanese Patent Publication No. SHO-60-55481 discloses that a pyrogenic substance such as calcium oxide is stored in the outer space of a double container and a mixture of an oily disinfestant and an organic blowing agent is stored in the inner space thereof. Water is added to the calcium oxide in the outer space to generate heat. The heat is used to heat up the organic blowing agent to 150 degree Celsius to cause it to blow. A large volume of nitrogen gas resulting from the decomposition of the blowing agent atomizes the disinfestant in the form of mist to kill insects. Main disinfestants include allethrin, phthalthrin, resmethrin and permethrin. The boiling points and decomposition points of all of these disinfestants are above 200 degree Celsius, and all of such disinfestants are oily. Organic blowing agents generate nitrogen through, for example, thermal decomposition. The blowing temperatures are around 200 degree Celsius for azodicarbonamide and dinitrosopentamethylenetetramine, around 150 degree Celsius for 1-butylazoformamide and benzenesulfonylhydrazideamide, and around 120 degree Celsius for paratoluenesulfonylhydrazide and 4,4'-azobis[cyanovaleric acid]. These blowing agents are heated up to 150 degree Celsius approx. by the exothermic reaction of the calcium oxide to blow. The oily disinfestant does not undergo thermal decomposition. It is atomized in the form of mist by the stream of nitrogen.

SUMMARY OF THE INVENTION

The tasks of the present invention are as follows:

1) To reproduce scents of new conveyances in used conveyances such as automobiles so as to refresh used conveyances in the aspect of scent to the conditions of new ones;

2) To perfume and at the same time to mask or cover up the irritating smell of a disinfestant with a fragrance liquid.

3) To prevent the fragrance liquid from being decomposed at the time of atomization, and to retain the scent of new conveyance for a long period.

The present invention rests in a method of perfuming conveyances wherein an oily fragrance liquid which emits the scent of new conveyance is mixed with an organic blowing agent, a pyrogenic agent is made to generate heat around the fragrance liquid inside the conveyance to make said blowing agent blow to atomize the fragrance liquid, and the atomized fragrance liquid is made to adhere to the interior or the conveyance. The present invention also rests in a perfuming article for conveyances wherein a double container is provided with at least a first chamber inside and a second chamber outside the first chamber, a mixture of an organic blowing agent, an oily disinfestant and an oily fragrance liquid emitting the scent of new conveyance is stored in the first chamber, a pyrogenic agent is stored in the second chamber, the first chamber and the second chamber are respectively provided with an opening, and a seal is provided to seal up such openings. Moreover, the present invention rests in a perfuming article for conveyances wherein a container has a third chamber around the first and second chambers, a mixture of an organic blowing agent and an oily fragrance liquid emitting the scent of new conveyance is stored in the first chamber, a mixture of the organic blowing agent and a deodorant is stored in the second chamber and a pyrogenic agent is stored in the third chamber, respectively, the first chamber, the second chamber and the third chamber are provided with an opening, respectively, and a seal is provided to close such openings.

Among various conveyances, automobiles are particularly important and are fit to be refreshed by used car dealers before the trade to have the scent of new ones. A fragrance liquid may be atomized alone. It, however, is desirable to atomize a fragrance liquid together with a disinfestant and/or a deodorant. Let us take a case wherein a disinfestant and a fragrance liquid are atomized together to explain the merits of the present invention. Conveyances such as automobiles have their unique scents, and it is intended to regain such scents through perfuming. When an oily fragrance liquid is used, its boiling point and decomposition point are generally high, and it may be mixed with an organic blowing agent for atomization. Popular disinfestants are mostly oily ones, and oily fragrance liquids may be mixed with such disinfestants. The heat from the surrounding pyrogenic agent makes the organic blowing agent decompose. As a result, the fragrance liquid will be atomized. As the oily fragrance liquids generally have high decomposition points, they will not be decomposed by the heating (to 100–200 degree Celsius) at the time of blowing. The atomized fragrance liquid will adhere to seats and the like. As its boiling point is high, it will evaporate gradually; thus the scent will last for one to six months. The fragrance liquid masks or covers up the irritating smell of the disinfestant, making it easier to disinfest the conveyance.

The inventor found that new conveyances have their unique scents and that the constituents of such scents may be represented by means of organic compounds having a benzene ring and oxygen atom and a perfuming constituent or constituents. The most typical organic compound having a benzene ring and oxygen atom is benzyl acetate. The scent of this substance is present in most new conveyances. Perfuming constituents are varied, ranging from natural scents, such as scents of plants like aromas of flowers and stalks, and musk, to synthetic ones such as that of benzyl benzoate. Such scents of new conveyances may be reproduced by blending. Typical perfuming substances include benzyl benzoate, rose oil, Iran—Iran oil, isoeugenol, neroli oil and oakmoss absolute. Appropriate perfuming constituents may be produced for most conveyances by varying the combinations of such substances.

BRIEF DESCRIPTION OF EMBODIMENTS OF THE DRAWINGS

FIG. 1 A cross-sectional view of the perfuming article of the first embodiment.

Figure 2:
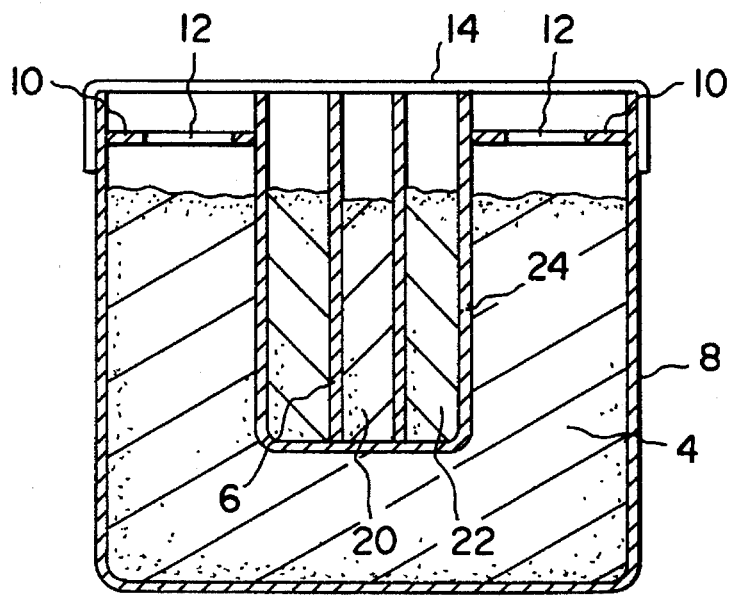

FIG. 2 A cross-sectional view of the perfuming article of the second embodiment.

BRIEF DESCRIPTION OF EMBODIMENTS OF THE INVENTION

Embodiment 1

FIG. 1 shows an embodiment wherein a fragrance liquid and a disinfestant are released at the same time. In the diagram, 2 is a mixture of an oily fragrance liquid, an oily disinfestant and an organic blowing agent, and 4 is powder calcium oxide. 4 may be a pyrogenic agent such as pure iron which is used in an inner portable heater. 6 is a metal container, and 8 is an outer metal container. 10 is a cover of the outer container, and 12 is an opening thereof. As illustrated in the diagram, the inner container 6 has an opening in its upper part. 14 is an impermeable seal made of metal-film-laminated paper, polyvinylidenechloride, etc. Table 1 through Table 4 show examples of oily fragrance liquids. Names of manufacturers and the names of vehicles are omitted. All of these fragrance liquids are oily, and they mix well with oily disinfestants and organic blowing agents. The boiling points of all the oily fragrance liquids are over 200 degree Celsius, and their decomposition points are over 240 degree Celsius. Desirable boiling points and decomposition points are over 180 degree Celsius, respectively, which prevents decomposition of such liquids when they are atomized, and assures that their effectiveness lasts over a long period. The quantity of an oily fragrance liquid is preferably from 5 to 30 grams per an automobile, and more preferably from 10 to 20 grams. Use of 10 to 20 grams will perfume an automobile with the scent of new automobile for one to six months.

Oily disinfestants may be the above- mentioned allethrin, phthalthrin, permethrin, etc., and various disinfestants may be used within the scope of prior art. It is desirable to use an disinfestant of which the odor is as weak as possible. The organic blowing agent may be the above-mentioned azodicarbonamide, benzenesulfonylhydrazide, paratoluenesulfonylhydrazide, etc. Hydration heat of calcium oxide 4 is utilized to blow the agent and in turn to atomize the disinfestant and the fragrance liquid.

Table 1

Table 1 Composition of a fragrance liquid (Japanese automobile A)

Constituent Content (weight percent) Remarks

Odoriferous constituents All the odoriferous constituents are natural ones.

Rose oil 13% Aroma of rose flower.

Musk 10% Scent of musk.

Iran—Iran oil 4.5% Aroma of flower.

Oakmoss absolute 2.5% Aroma of flower.

Other constituents

Benzyl acetate 70% CH3COOCH2C6H5 Boiling point: 215 degree Celsius.

Odor of ester solvent.

Table 2

Table 2 Composition of a fragrance liquid (U. S. automobile A)

Constituent Content (weight percent) Remarks

Odoriferous constituents All the odoriferous constituents are natural ones.

Iran—Iran oil 30% Aroma of flower.

Rose oil 12% Aroma of rose flower,

Oakmoss absutate 5% Aroma of flower.

Neroli oil 3% Aroma of stalk of a plant.

Other constituents

Benzyl acetate 25% CH3COOCH2C6H5 Boiling point: 215 degree Celsius.

Phenylethyl alcohol 10% C6H5CH(OH)CH3 Boiling point: 219 degree Celsius.

Cinnamic alcohol 10% C6H5CH=CHCH2OH Boiling point: 257 degree Celsius.

α-hexylcinnamaldehyde 5% C6H5CH=C[(CH2)5CH3]CHO Boiling point: 129 degree Celsius.

Table 3

Table 3 Composition of a fragrance liquid (German automobile manufacturer A)

Constituent Content (weight percent) Remarks

Odoriferous constituents The odoriferous constituents are synthetic ones.

Benzyl benzoate 10% Smell of rubber. C6H5COOCH2C6H5

Isoeugenol 5% Burnt smell—stuffy smell. CH3OC6H3(CH=CHCH3)OH Other constituents

Benzyl acetate 55% CH3COOCH2C6H5

Benzyl salicylate 15% C6H4OHCOOCH2C6H5 p-cresylphenyl acetic acid 5% C6H4(CH3)COOCH2C6H5

Cinnamic alcohol 5% C6H5CH=CHCH2OH

α-hexylcinnamaldehyde 5% C6H5CH=C[(CH2)5CH3]CHO

Table 4

Table 4 Composition of a fragrance liquid (German automobile manufacturer B)

Constituent Content (weight percent) Remarks

Odoriferous constituents

Benzyl benzoate 20% Smell of rubber.

Isoeugenol 10% Burnt smell—stuffy smell. Other constituents

Benzyl acetate 50% CH3COOCH2C6H5

Methyl salicylate 10% C6H4(OH)(COOCH3)

Isoamyl acetate 10% (CH3)2CHCH2CH2COOCH3

* Isoamyl acetate alone is nonaromatic.

All others are benzene derivative compounds with oxygen.

The fragrance liquids of Table 1 through Table 4 are blended to give automobiles of the four manufacturers scents identical to those of the respective new automobiles. As clearly seen from Table 1 through Table 4, the fragrance liquids have two groups of constituents; odoriferous constituents and other constituents. The group of the other constituents is all aromatic compounds combined with oxygen, except isoamyl acetate of the liquid for the German automobile B. The aromatic compounds are basically phenyl groups, and the oxygen is contained in the form of ester group, hydroxyl group, aldehyde group or carboxyl group. The constituents of the other group correspond to the smells of solvents contained in various plastics, coating materials, lubricants, adhesives, etc. of the automobiles. One common item is benzyl acetate. The smell of this constituent is contained in all the scents of the new automobiles of the four manufacturers.

The odoriferous constituents for the Japanese automobile A of Table 1 and the U.S. automobile A of Table 2 correspond to scents of flowers and musk. These constituents are natural odoriferous substances, and the inclusion of such scents indicates that the automobile manufacturers intentionally perfume their automobiles. On the other hand, the scents of the German automobiles A and B of Tables 3 and 4, respectively, correspond to smells generated from organic solvents, adhesives, etc. They are not scents intentionally added, but rather are the smells of the automobile plants and the parts of automobiles. For instance, benzyl benzoate corresponds to the smell of rubber, and isoeugenol corresponds to a burning and stuffy smell. Such smells are mechanical and heavy ones and are directly opposite to the graceful scents of plants employed in the Japanese and U.S. automobiles.

The compositions shown in Table 1 through Table 4 are just examples. There are many other combinations of odoriferous constituents that give the identical scents in a sensory test. Such combinations may be determined by blending. Next, scents of new automobiles are mainly determined by automobile manufacturers. It, therefore, is desirable to determine the compositions of odoriferous constituents for the respective automobile manufacturers or for larger groups of manufacturers based on regions, such as the U.S., Japanese and European auto manufacturers. The compositions of odoriferous constituents may be more finely determined for the respective kinds of automobiles. Moreover, a scent which differs from the genuine scent of a new car may be used. For instance, a scent of a Japanese automobile may be given to a German one.

Merits of the embodiment will be explained in the following. An oily fragrance liquid mixes well with an oily disinfestant and an oily organic blowing agent. The mixture may be preserved over a long period without separation. The mixture of these three kinds of substances 2 is stored in the inner container 6. A pyrogenic agent such as calcium oxide 4 is contained in the outer container 8. The seal 14 prevents moisture from penetrating into the containers. When a used car is perfumed with the scent of new car before trade by a dealer of used cars, the doors and windows of the automobile are closed, and the ashtray of the cigarlighter will be drawn out. The perfuming article is placed on the ashtray, and the seal 14 is pealed off. Water is poured into the opening 12. Then the calcium oxide 4 generates heat. The mixture 2 is heated to, for example, about 150 degree Celsius. The nitrogen gas, which is released by the decomposition of the organic blowing agent, atomizes the fragrance liquid and the disinfestant in the form of mist. The atomized fragrance liquid and disinfestant adhere to the interior of the automobile.

The use of the disinfestant is to disinfect the used automobile before trade. The smell of the disinfestant is, at least, partly covered up by the fragrance liquid. Moreover, as the disinfestant is highly active, it decomposes earlier than the fragrance liquid. Hence, when the windows are opened up after disinfestation, the smell of the disinfestant will almost disappear in a day or so. Thus the disinfestation and perfuming may be done immediately before the trade. After one day or so, only the scent of the fragrance liquid will remain. The fragrance liquid, which is atomized in the form of mist, penetrates mainly into the fabric parts and leather parts, such as seats, of the automobile, and adheres to them intact in the form of mist. This is because the boiling point and the decomposition point of the fragrance liquid are above 200 degree Celsius. At the time of blowing, it does not undergo thermal decomposition. It is atomized in the form of mist, and it sticks to the interior of the automobile. The fragrance liquid sticking to the interior of the automobile evaporates gradually to give the scent. The lasting time of this scenting is about one month when the quantity of the fragrance liquid is set as mentioned above. The scent of new car will remain for about six months for a person with a keen sense of smell.

With the above-mentioned effects, the used car is disinfested, and the scent of the car is restored to that of new car. The used car is refreshed in the aspect of scent to the state of the new car. The fragrance liquid masks or covers up the smell of the disinfestant and weakens the irritating smell generated by the disinfestant. Thus when the trade of a used car is decided, the car may be disinfested and perfumed to sell. In the present embodiment the fragrance liquid and the disinfestant are used in mixture. The fragrance liquid alone, however, may be atomized by the organic blowing agent.

Embodiment 2

FIG. 2 shows the second embodiment. It differs from the embodiment of FIG. 1 in that a deodorant is used in place of the disinfestant. 20 denotes a mixture of an oily fragrance liquid and an organic blowing agent. 22 is a mixture of a deodorant and an organic blowing agent. 24 is an intermediate container located between an inner container 6 and an outer container 8. The organic blowing agent to be mixed with the oily fragrance liquid may be one with a blowing temperature of about 150 degree Celsius, for example, 1-butylazoformamide. The organic blowing agent to be mixed with the deodorant may be one with a blowing temperature of about 150 degree Celsius, for example, paratoluenesulfonylhydrazide. The deodorant may be an clathrate compound, such as methacrylate laurate and phenylisothiocyanate. The oily fragrance liquid is used in excess relative to the deodorant so that even if all of the deodorant reacted with the fragrance liquid, some of the fragrance liquid would remain intact without being deodorized. In the present embodiment, the deodorant can deodorize from 5 to 20% of the fragrance liquid.

The merits of the embodiment of FIG. 2 will be explained in the following. In the same way as the embodiment of FIG. 1, a perfuming article is placed on an ashtray of a cigar-lighter inside the automobile with doors and windows closed. A seal 14 is peeled off, and water is added to calcium oxide 4 to generate heat. The heat of hydration is first transmitted to the mixture 22 of the organic blowing agent and the deodorant contained in the middle container 24, and the deodorant is atomized first. When the decomposition of the blowing agent in the intermediate container is completed, the heat is transmitted to the mixture 20 of the organic blowing agent and the oily fragrance liquid contained in the inner container 6, and the oily fragrance liquid will be released. This arrangement, namely, the fragrance liquid is atomized only after the deodorant has been atomized, is intended to make perfuming only after deodorization. To this end, a blowing agent which blows at a lower temperature is used for the deodorant, and another blowing agent which blows at a higher temperature is used for the fragrance liquid. Thus a time lag is introduced between the two blowings. The heat from the calcium oxide 4 is first applied to the blowing agent of the deodorant contained in the intermediate container 24. As the blowing is accompanied by an endothermism, the blowing agent on the fragrance liquid side does not get heat and does not blow until the blowing agent on the deodorant side is completely decomposed. In the present embodiment, two arrangements are used to produce time lag between the blowings of the two blowing agents (1) that the blowing temperatures of the two blowing agents are varied from each other, and (2) that a triple container is used wherein the fragrance liquid is placed in the innermost part thereof. It, however, is possible to have a time lag by means of the configuration of the container while a common blowing temperature is used on both the deodorant side and the fragrance liquid side. Moreover, it is possible to have a time lag between the two blowings by means of the difference between the two blowing temperatures.

The atomized deodorant eliminates the smells in the automobile, and the excessive deodorant adheres to the interior of the automobile. Next, the fragrance liquid is atomized. It adheres to the interior of the automobile to perfume. The atomized deodorant has been consumed to eliminate the smell present inside the automobile. Moreover, as the fragrance liquid is used in excess relative to the deodorant, the greater part of the fragrance liquid is not deodorized and is utilized for perfuming. As a result, the interior of the automobile is firstly deodorized, and then the scent of the new automobile is provided by the fragrance liquid to attach to the interior for one to six months. In the embodiment of FIG. 2, the mixture of the deodorant and the blowing agent is stored in the intermediate container, but a mixture of a deodorant, a disinfestant and a blowing agent may be used in place of the former.

We claim:

1. A method of perfuming vehicles, comprising mixing an oily fragrance liquid which emits the scent of a new vehicle, said oily fragrance liquid comprising at least two perfuming ingredients which together are capable of providing the scent of a new vehicle with an organic blowing agent, generating heat around the fragrance liquid inside a vehicle by activating a pyrogenic agent so as to make said blowing agent blow to atomize the fragrance liquid and make the atomized fragrance liquid adhere to the interior of the vehicle, thereby perfuming the vehicle.

2. A method of perfuming vehicles as recited in claim 1, wherein said fragrance liquid and an oily disinfestant are mixed with said organic blowing agent so that disinfestation and perfuming are effected while the smell of the disinfestant is covered up by the scent of said fragrance liquid.

3. A method of perfuming vehicles as recited in claim 1, further comprising mixing a deodorant with a second organic blowing agent, and blowing the second blowing agent before blowing the other said blowing agent so that the vehicle is perfumed only after it was deodorized.

4. A method of perfuming vehicles as recited in claim 1, wherein the fragrance liquid has a boiling point and a decomposition point over 180 degrees Celsius.

5. A method of perfuming vehicles as recited in claim 4, wherein at least a part of said fragrance liquid is made to adhere to fabric parts or leather parts inside the vehicle and after perfuming the fragrance liquid is made to gradually vaporize to generate the scent of a new vehicle.

6. A method of perfuming vehicles as recited in claim 5, wherein said fragrance liquid contains organic compounds having a benzene ring and oxygen and odoriferous constituents.

7. A method of perfuming vehicles as recited in claim 6, wherein said organic compounds having a benzene ring and oxygen include at least benzyl acetate, and said odoriferous constituents include at least one from benzyl benzoate, rose oil, Iran—Iran oil, isoeugenol, neroli oil and oakmoss absolute.

8. A perfuming article for vehicles comprising at least a double container having a first inner chamber and a second outer chamber, a mixture of an organic blowing and an oily fragrance liquid capable of emitting the scent of new vehicle being stored in the first chamber, a pyrogenic agent being stored in the second chamber, the first chamber and the second chamber each having an opening and seals to close the respective openings.

9. A perfuming article for vehicles comprising a container having a first inner chamber, a second middle chamber and a third outer chamber located around the first and second chambers, a mixture of an organic blowing agent and an oily fragrance liquid capable of emitting the scent of new vehicle being stored in the first chamber, a mixture of an organic blowing agent and a deodorant being stored in the second chamber, a pyrogenic agent being stored in the third chamber, the first chamber, the second chamber and the third chamber each having an opening and seals to close the respective openings.

10. A perfuming article for vehicles as recited in claim 9, wherein the blowing temperature of the organic blowing agent of the first chamber is higher than the blowing temperature of the organic blowing agent of the second chamber.

* * * * *